United States Patent
Han

(10) Patent No.: US 6,376,720 B1
(45) Date of Patent: Apr. 23, 2002

(54) COBALT-CATALYZED PROCESS FOR PREPARING 1,3-PROPANEDIOL

(75) Inventor: Yuan-Zhang Han, West Chester, PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/882,346

(22) Filed: Jun. 15, 2001

(51) Int. Cl.$^7$ .............................................. C07C 45/50
(52) U.S. Cl. ...................... 568/483; 568/862; 568/867
(58) Field of Search ................................. 568/451, 454, 568/852, 867, 854, 485, 862, 483

(56) References Cited

U.S. PATENT DOCUMENTS

| | | |
|---|---|---|
| 3,239,569 A | 3/1966 | Slaugh et al. |
| 4,096,188 A | 6/1978 | Wilkes |
| 5,463,144 A | 10/1995 | Powell et al. |
| 5,463,145 A | 10/1995 | Powell et al. |
| 5,463,146 A | 10/1995 | Slaugh et al. |
| 5,545,765 A | 8/1996 | Slaugh et al. |
| 5,545,767 A | 8/1996 | Weider et al. |
| 5,563,302 A | 10/1996 | Weider et al. |
| 5,576,471 A | 11/1996 | Semple et al. |
| 5,585,528 A | 12/1996 | Powell et al. |
| 5,723,389 A | 3/1998 | Slaugh et al. |
| 5,731,478 A | 3/1998 | Slaugh et al. |
| 5,770,776 A | 6/1998 | Powell et al. |
| 5,786,524 A | 7/1998 | Powell et al. |
| 5,841,003 A | 11/1998 | Slaugh et al. |
| 5,981,808 A | 11/1999 | Powell et al. |

*Primary Examiner*—Sreeni Padmanabhan
(74) *Attorney, Agent, or Firm*—William C. Long

(57) ABSTRACT

Ethylene oxide is hydroformylated to 3-hydroxypropanal using a non-phosphine-ligated cobalt catalyst and diamine promoter.

5 Claims, 1 Drawing Sheet

COBALT-CATALYZED PROCESS FOR PREPARING 1,3-PROPANEDIOL

BACKGROUND OF THE INVENTION

This invention relates to the preparation of 1,3-propanediol, especially to a cobalt-catalyzed process for manufacturing 1,3-propanediol in high yields without the use of a phosphine ligand for the cobalt catalyst.

1,3-Propanediol (PDO) is an intermediate in the production of polyesters for fibers and films. It is known to prepare PDO in a two-step process involving (1) the cobalt-catalyzed hydroformylation (reaction with synthesis gas, $H_2/CO$) of ethylene oxide to intermediate 3-hydroxypropanal (HPA) and (2) subsequent hydrogenation of the HPA to PDO. The initial hydroformylation process can be carried out at temperatures greater than 100° C. and at high syngas pressures to achieve practical reaction rates. The resulting product mixture is, however, rather unselective for HPA.

Alternatively, the cobalt catalyst has been used in combination with a phosphine ligand to prepare HPA with greater selectivity and at lower temperature and pressure. However, the use of a phosphine ligand adds to the cost of the catalyst and increases the complexity of catalyst recycle.

There are a number of prior art references which relate to 1,3-propanediol production including the step of hydroformylation of ethylene oxide using a cobalt catalyst in the absence of a phosphine ligand, using other ligands. See, for example, the following U.S. Patents: U.S. Pat. Nos. 5,981,808, 5,463,145, 5,463,146, 5,545,767, 5,731,478, 5,723,389, 5,786,524, 5,841,003, 5,576,471, 5,563,302, 5,545,765, 5,463,144, 5,770,776 and 5,585,528.

U.S. Pat. No. 4,096,188 describes the preparation of straight chain olefins by catalytic hydroformylation with carbon monoxide and hydrogen in the presence of cobalt catalyst and primary secondary or tertiary amine modifier.

SUMMARY OF THE INVENTION

According to the present invention, 1,3-propanediol is prepared in a process which comprising contacting ethylene oxide with carbon monoxide and hydrogen in the presence of an effective amount of a non-phosphine-ligated cobalt catalyst and an effective amount of a diamine promoter at conditions effective to form 3-hydroxypropanal. It is especially advantageous to use a lipophillic diamine and to employ a non-water miscible solvent. Usually the reaction conditions comprise a temperature within the range of about 50° to about 100° C. and a pressure within the range of about 500 to about 5000 psi. Conveniently, an aqueous liquid can be added to the intermediate product mixture at less than about 100° C. in order to extract a major portion of the 3-hydroxypropanal into the aqueous phase and to provide an organic phase comprising at least a portion of the cobalt catalyst or a cobalt-containing derivative thereof and at least a portion of the diamine promoter. The phases can be separated and the aqueous phase comprising 3-hydroxypropanal hydrogenated to produce the 1,3-propandiol product.

The process enables the production of 1,3-propanediol in high yields and selectivity without the use of a phosphine ligated cobalt catalyst in the hydroformylation step. The process also enables the recovery and recycle of essentially all the cobalt catalyst.

DETAILED DESCRIPTION OF THE INVENTION

Figure 1:
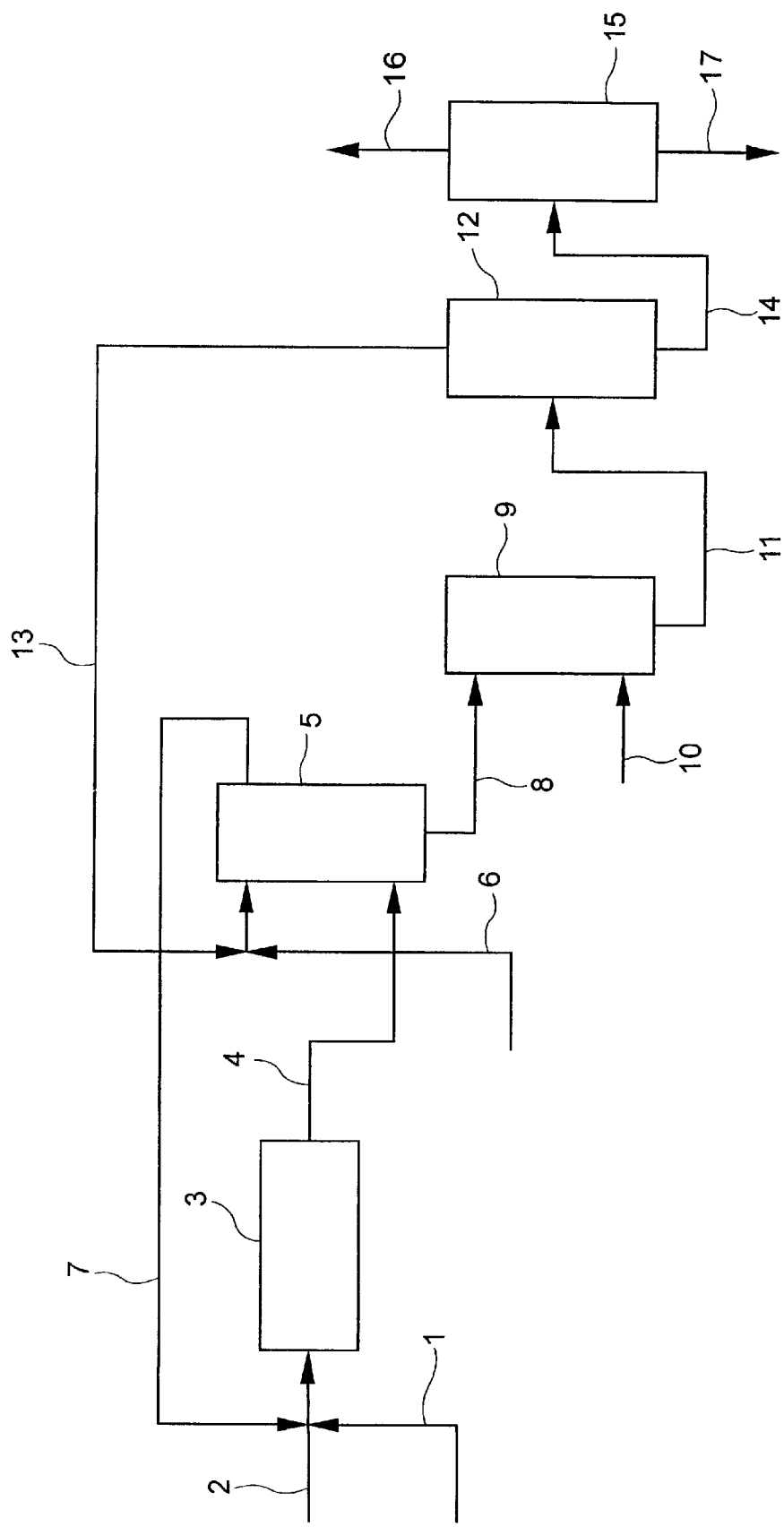
FIG. 1 is a schematic flow diagram of one embodiment of the invention 1,3-propanediol preparation process.

With the exception of the promoter employed herein the process and reaction conditions are essentially the same as employed in prior art such as U.S. Pat. No. 5,585,528.

The process of the invention can be conveniently described by reference to FIG. 1. Separate or combined streams of ethylene oxide introduced via line 1, carbon monoxide and hydrogen introduced via line 2 are charged to hydroformylation vessel 3, which can be a pressure reaction vessel such as a bubble column or agitated tank, operated batch wise or in a continuous manner. The feed streams are contacted in the presence of a non-phosphine-ligated cobalt catalyst, i.e., a cobalt carbonyl composition which has not been prereacted with a phosphine ligand. The hydrogen and carbon monoxide will generally be introduced into the reaction vessel in a molar ratio within the range of about 1:2 to about 8:1, preferably about 1.5:1 to about 5:1.

The reaction is carried out under conditions such as used in the art effective to produce a hydroformylation reaction product mixture containing a major portion of 3-hydroxypropanal (HPA) and a minor portion of acetaldehyde, while maintaining the level of 3-hydroxypropanal in the reaction mixture at less than 15 wt %, preferably within the range of about 5 to about 10 wt %. (To provide for solvents having different densities, the desired concentration of HPA in the reaction mixture can be expressed in morality, i.e. less than 1.5M, preferably within the range of about 0.5 to about 1M). Generally, the hydroformylation reaction is carried out at elevated temperature less than 100° C., preferably about 60° to about 90° C., most preferably about 75° to about 85° C., and at a pressure within the range of about 500 to 5000 psi, preferably (for process economics) about 1000 to about 3500 psi. The concentration of 3-hydroxypropanal in the intermediate product mixture can be controlled by regulation of process conditions such as ethylene oxide concentration, catalyst concentration, reaction temperature and residence time. In general, relatively low reaction temperatures (below about 90° C.) and relatively short residence times (about 20 minutes to about 1 hour) are preferred. In the practice of the invention method, it is possible to achieve HPA yields (based on ethylene oxide converted) of greater than 80%, with formation of greater than 7 wt % HPA, at rates greater than 30 $h^{-1}$. (Catalytic rates are referred to herein in terms of "turnover frequency" or "TOF" and are expressed in units of moles per mole of cobalt per hour, or $h^{-1}$). Reported rates are based on the observation that before a majority of the ethylene oxide is converted, the reaction is essentially zero-order in ethylene oxide concentration and proportional to cobalt concentration.

The hydroformylation reaction is carried out in a liquid solvent inert to the reactants. By "inert" is meant that the solvent is not consumed during the course of the reaction. In general, ideal solvents for the phosphine ligand-free process will solubilize carbon monoxide, will be essentially nonwater-miscible and will exhibit low to moderate polarity such that the 3-hydrozypropanal intermediate will be solubilized to the desired concentration of about 5 wt % under hydroformylation conditions, while significant solvent will remain as a separate phase upon water extraction. By "essentially nonwater-miscible" is meant that the solvent has a solubility in water at 25° C. of less that 25 wt % so as to form a separate hydrocarbon-rich phase upon water extraction of HPA from the hydroformylation reaction mixture. Preferably this solubility is less than 10 wt %, most preferably less than about 5 wt %. The solubilization of carbon monoxide in the selected solvent will generally be greater than 0.15 v/v (1 atm, 25° C.), preferably greater than 0.25 v/v, expressed in terms of Ostwald coefficients.

The preferred class of solvents are alcohols and ethers such are as described in said U.S. Pat. No. 5,585,528. Ethers such as methyl-t-butyl ether, ethyl-t-butyl ether, ethoxyethyl ether, diethyl ether phenyl isobutyl ether, diphenyl ether and diisopropyl ether are useful. Blends of solvents such as tetrahydrofuran/toluene, tetrahydrofuran/heptane and t-butyl alcohol/hexane can also be used to achieve the desired solvent properties. The currently preferred solvent, because of the high yields of HPA which can be achieved under moderate reaction conditions, is methyl-t-butyl ether.

The catalyst is a non-phosphine-ligated cobalt carbonyl compound. The cobalt catalyst can be supplied to the hydroformylation reactor in essentially any form including metal, supported metal, Raney-cobalt, hydroxide, oxide, carbonate, sulfate, acetylacetonate, salt of a fatty acid, or as an aqueous cobalt salt solution, for example. It may be supplied directly as a cobalt carbonyl such as dicobaltoctacarbonyl or cobalt hydridocarbonyl. If not supplied in the latter forms, operating conditions can be adjusted such that cobalt carbonyls are formed in situ via reaction with $H_2$ and CO, as described in J. Falbe, "Carbon Monoxide in Organic Synthesis", Springer-Verlag, N.Y. (1970). In general, catalyst formation conditions will include a temperature of at least 50° C. and a carbon monoxide partial pressure of at least about 100 psi. For more rapid reaction, temperatures of about 120° to 200° C. should be employed, at CO pressures of at least 500 psi. Addition of high surface area activated carbons or zeolites, especially those containing or supporting platinum or palladium metal, can accelerate cobalt carbonyl formation from noncarbonyl precursors. The resulting catalyst is maintained under a stabilizing atmosphere of carbon monoxide, which also provides protection against exposure to oxygen. The most economical and preferred catalyst activation and reactivation (of recycled catalyst) method involves performing the cobalt salt (or derivative) under $H_2$/CO in the presence of the catalyst promoter employed for hydroformylation. The conversion of $Co^{+2}$ to the desired cobalt carbonyl is carried out at a temperature within the range of about 75° to about 200° C., preferably about 100° to about 140° C. and a pressure within the range of about 1000 to about 5000 psig for a time preferably less than about 3 hours. The performing step can be carried out in a pressurized performing reactor or in situ in the hydroformylation reactor.

The amount of cobalt present in the reaction mixture will vary depending upon the other reaction conditions, but will generally fall within the range of about 0.05 to about 0.3 wt %, based on the weight of the reaction mixture.

The hydroformylation reaction mixture will include a diamine promoter to accelerate the rate without imparting hydrophilicity (water solubility) to the active catalyst; preferably lipophillic diamine promoter is used. By "lipophillic" is meant that the diamine tends to remain in the organic phase after extraction of HPA with water. The diamine will be present in an amount effective to promote the hydroformylation reaction to HPA, generally an amount within the range of about 0.01 to about 0.6 moles, based on cobalt.

Suitable diamines include those represented by formula (1):

In which each of $R_1$, $R_2$, $R_3$ and $R_4$ is independently selected from hydrogen or from unsubstituted and non-interfering substituted $C_{1-25}$ hydrocarbyl groups. Q is any bridge connecting two amino groups with 2 or more covalent bonds.

Suitable diamines include N,N,N',N'-tetramethyldiamino methane, 1,8-bis(dimethylamino) naphthalene, and 2-dimethylaminopyridine.

It is generally preferred to regulate the concentration of water in the hydroformylation reaction mixture, as excessive amounts of water reduce (HPA+PDO) selectivity below acceptable levels and may induce formation of a second liquid phase. At low concentrations, water can assist in promoting the formation of the desired cobalt carbonyl catalyst species. Acceptable water levels will depend upon the solvent used, with more polar solvents generally more tolerant of higher water concentrations. For example, optimum water levels for hydroformylation in methyl-t-butyl ether solvent are believed to be within the range of about 1 to about 2.5 wt %.

Following the hydroformylation reaction, hydroformylation reaction product mixture 4 containing 3-hydroxypropanal, the reaction solvent, 1,3-propanediol, the cobalt catalyst, diamine promoter and a minor amount of reaction by-products, is passed to extraction vessel 5, wherein an aqueous liquid, generally water and optional miscibilizing solvent, are added via 6 for extraction and concentration of the HPA for the subsequent hydrogenation step. Liquid extraction can be effected by any suitable means, such as mixer-settlers, packed or trayed extraction columns, or rotating disk contactors. Extraction can if desired be carried out in multiple stages. The water-containing hydroformylation reaction product mixture can optionally be passed to a settling tank (not shown) for resolution of the mixture into aqueous and organic phases. The amount of water added to the hydroformylation reaction product mixture will generally be such as to provide a water mixture ratio with the range of about 1:1 to about 1:20, preferably about 1:5 to about 1:15. The addition of water at this stage of the reaction may have the additional advantage of suppressing formation of undesirable heavy ends. Extraction with a relatively small amount of water provides an aqueous phase which is greater than 35 wt % HPA, permitting economical hydrogenation of the HPA to PDO. The water extraction is preferably carried out at a temperature within the range of about 25° to about 55° C., with higher temperatures avoided to minimize condensation product (heavy ends) and catalyst disproportionate to inactive, water-soluble cobalt species. In order to maximize catalyst recovery, it is optional but preferred to perform the water extraction under 50–200 psig carbon monoxide.

The organic phase containing the reaction solvent and the major portion of the cobalt catalyst can be recycled from the extraction vessel to the hydroformylation reaction via line 7. Aqueous extract is removed via line 8 is optionally passed through one or more acid ion exchange resin beds (not shown) for removal of any cobalt catalyst present, and the decobalted aqueous product mixture is passed to hydrogenation vessel 9 and reacted with hydrogen 10 in the presence of a hydrogenation catalyst to produce a hydrogenation product mixture containing 1,3-propanediol. The hydrogenation step may also revert some heavy ends to PDO. The hydrogenation product passes via line 11 to separation zone 12. The solvent and extractant water can be recovered by distillation and recycled via line 13 to the water extraction process, via a further distillation (not shown) for separation and purge of light ends. The PDO-containing stream 16 is passed to distillation column 15 for recovery of PDO via line 16 from heavy ends which are removed via line 17.

Hydrogenation of the HPA to PDO can be carried out in aqueous solution at an elevated temperature of a least about 40° C., generally within the range of about 50° to about 175° C., under a hydrogen pressure of at least about 100 psi, generally within the range of about 200 to about 2000 psi. The reaction is carried out in the presence of a hydrogenation catalyst such as any of those based upon Group VIII metals, including nickel, cobalt, ruthenium, platinum and palladium, as well as copper, zinc and chromium. Nickel catalysts, including bulk, supported and fixed-bed forms, provide acceptable activities and selectivities at moderate cost. Highest yields are achieved under slightly acidic reaction conditions.

Commercial operation will require efficient cobalt catalyst recovery with essentially complete recycle of cobalt to the hydroformylation reaction. The preferred catalyst recovery process involves two steps, beginning with the above described water extraction of HPA under carbon monoxide from the hydroformylation product mixture. A majority of the cobalt catalyst will remain in the organic solvent phase, with the remaining cobalt catalyst passing into the water phase. The organic phase can be recycled to the hydroformylation reactor, with optional purge of heavy ends. Optional further decobalting of catalyst in the water layer can be effected by suitable method, such as complete or partial oxidation of cobalt followed by precipitation and filtration, distillation, deposition on a solid support, or extraction using a suitable extractant, preferably prior to final cobalt removal by ion exchange.

The invention process permits the selective and economic synthesis of PDO at moderate temperatures and pressures without the use of a phosphine ligand for the hydroformylation catalyst. The process involves preparation of a reaction product mixture dilute in intermediate HPA, then concentration of this HPA by water extraction followed by hydrogenation of the aqueous HPA to PDO.

EXAMPLE 1
(Comparative)

$Co_2(CO)_8$ (0.93 g), 120 g methyl t-butyl ether, 1.5 g toluene (internal GC standard), 2.0 g distilled water was charged into a 300 ML Parr reactor. The reactor was pressurized with nitrogen and pressure was released to remove any air in the system. The nitrogen atmosphere was flushed with hydrogen and the reactor was filled with 600 psi hydrogen, then pressurized to 900 psig with syngas (CO/H2=1/1). The reactor content was heated to 120° for 1 hr, then cooled to 80° C. 11.2 g ethylene oxide was then injected with syngas pressure gas (CO/H2=1/1) and the reactor pressure was reached 1400 psig. More syngas was added to maintain the pressure between 1200 to 1400 psig as the syngas gets consumed. The reactor content was analyzed with on-line GC. The turnover frequency (TOF) relative to Co was 33 $h^{-1}$ during the first 30 min of the reaction. After the reaction was continued for 2 h, the reactor was cooled to room temperature and 20 g distilled water was added to approximately 60–70 g the reactor content from the above reaction. Water extraction was carried out under nitrogen atmosphere. The water extract was run through a resin bed and then hydrogenated with Raney Nickel under 1000 psig H2 and at 120° C. maximum temperature. The overall selectivities to 1,3-propanediol, n-propanol, and ethanol from hydroformylation and hydrogenation processes are 85%, 1% and 14% respectively.

EXAMPLE 2
(Comparative)

Example 1 was repeated except that 0.47 equiv (relative to Co) of dimethyldodecylamine was added to the hydroformylation reactor as promoter. The turnover frequency (TOF) relative to Co was 55 $h^{-1}$ during the first 30 minutes of the reaction.

EXAMPLE 3
(Comparative)

Example 1 was repeated except that 0.47 equiv (relative to Co) of 4-benzyl pyridine was added to the hydroformylation reactor as promoter. The turnover frequency (TOF) relative to Co was 87 $h^{-1}$ during the first 30 minutes of the reaction.

EXAMPLE 4

Example 1 was repeated except that 0.06 equiv 1,8-bis (dimethylamino)naphthalene (N/Co molar ratio=0.12) was added to the hydroformylation reactor as promoter. The turnover frequency (TOF) relative to Co was 55 $h^{-1}$ during the first 30 min. of the reaction.

EXAMPLE 5

Example 1 was repeated except that 0.27 equiv 2-dimethylaminopyridine (N/Co molar ratio=0.54) was added to the hydroformylation reactor as promoter. The turnover frequency (TOF) relative to Co was 98 $h^{-1}$ during the first 30 min. of the reaction.

The above results demonstrate the effectiveness of diamines in promoting the hydroformylation reaction. Other diamines provide similar results.

I claim:

1. A process for preparing 3-hydroxypropanal comprising contacting ethylene oxide with carbon monoxide and hydrogen at reaction conditions in the presence of an effective amount of a non-phosphine-ligated cobalt catalyst and an effective amount of a diamine promoter having the formula: $R_1R_2NQNR_3R_4$, each of $R_1$, $R_2$, $R_3$ and $R_4$ being selected from hydrogen or from unsubstituted and non-interfering substituted $C_{1-25}$ hydrocarbyl groups and Q is a bridge connecting two amino groups with two or more covalent bonds.

2. The process of claim 1 wherein the said 3-hydroxypropanal is hydrogenated to 1,3-propanediol.

3. The process of claim 1 wherein the promoter is N,N,N',N'-tetramethyldiamine methane.

4. The process of claim 1 wherein the promoter is 1,8-bis(dimethylamino) naphthalene.

5. The process of claim 1 wherein the promoter is 2-dimethylaminopyridine.

* * * * *